United States Patent [19]

Ueno et al.

[11] Patent Number: 4,780,567

[45] Date of Patent: Oct. 25, 1988

[54] PROCESS FOR PRODUCING AROMATIC HYDROXYCARBOXYLIC ACIDS

[75] Inventors: Ryuzo Ueno, Nishinomiya; Toshiharu Kanagae, Kuwana; Mitsuyuki Kishimoto, Yokkaichi, all of Japan

[73] Assignee: Kabushiki Kaisha Ueno Seiyaku Oyo Kenkuyo, Osaka, Japan

[21] Appl. No.: 887,037

[22] PCT Filed: Nov. 9, 1985

[86] PCT No.: PCT/JP85/00626

§ 371 Date: Jul. 1, 1986

§ 102(e) Date: Jul. 1, 1986

[87] PCT Pub. No.: WO86/02924

PCT Pub. Date: May 22, 1986

[30] Foreign Application Priority Data

Nov. 9, 1984 [JP] Japan ............................ 59-235033

[51] Int. Cl.$^4$ ............................................ C07L 51/15
[52] U.S. Cl. ................................ 562/425; 562/423; 562/424
[58] Field of Search ..................... 562/423, 424, 425

[56] References Cited

U.S. PATENT DOCUMENTS

| | | | |
|---|---|---|---|
| 2,132,356 | 10/1938 | Lecher et al. | 260/523 |
| 2,132,357 | 10/1938 | Lecher et al. | 260/111 |
| 4,239,913 | 12/1980 | Ueno et al. | 562/424 |
| 4,297,508 | 10/1981 | Maegawa et al. | 562/425 |

FOREIGN PATENT DOCUMENTS

| | | | |
|---|---|---|---|
| 0053824 | 6/1982 | European Pat. Off. | |
| 9164751 | 9/1984 | Japan | 562/424 |
| 1342508 | 1/1974 | United Kingdom | |
| 2008090 | 5/1979 | United Kingdom | |

OTHER PUBLICATIONS

Alan S. Lindsey and Harold Jeskey, "The Kolbe-Schmitt Reaction", *Chemical Reviews*, vol. 57, No. 4, pp. 583–620 (Aug. 1957).

*Primary Examiner*—Paul J. Killos
*Attorney, Agent, or Firm*—Sherman and Shalloway

[57] ABSTRACT

This invention provides a process for selectively producing aromatic hydroxycarboxylic acids, which comprises subjecting a liquid mixture consisting of a polycyclic aromatic hydrocarbon, an alkali metal salt of an aromatic hydroxy compound and a free aromatic hydroxy compound to a reaction with carbon dioxide. The process permits the production of the intended product with enhanced selectivity.

5 Claims, 1 Drawing Sheet

PROCESS FOR PRODUCING AROMATIC HYDROXYCARBOXYLIC ACIDS

FIELD OF TECHNOLOGY

This invention relates to a process for selectively producing aromatic hydroxycarboxylic acids, which comprises liquefying an alkali metal salt of an aromatic hydroxy compound with an added aromatic hydroxy compound, followed by reaction with carbon dioxide in a liquid-liquid mixture with a medium.

BACKGROUND TECHNOLOGY

Aromatic hydroxycarboxylic acids, particularly p-hydroxybenzoic acid, salicylic acid, 2-hydroxy-3-naphthoic acid, etc., have long been known for their usefulness as raw materials for the production of antiseptic and antifungal agents, pharmaceuticals, dyestuffs, pigments and the like, and in recent years, have furthermore acquired increasingly greater importance not only as starting compounds for the synthesis of agricultural chemicals, color developing agents for thermosensitive recording paper, etc. but also as monomers for aromatic polyesters.

These aromatic hydroxycarboxylic acids have conventionally been produced by means of the so-called Kolbe-Schmitt process involving a vapor-solid phase reaction of an alkali metal salt of aromatic hydroxy compound with carbon dioxide. Lately, one of the present inventors has improved the said vapor-solid phase reaction process into the liquid-solid phase reaction process making use of a suspension phase, and thus, there has been established a process which permits an industrial-scale, mass-production of such aromatic hydroxycarboxylic acids [refer to the specification of Patent Application No. 39281/1983 (Laid-Open Patent Publication No. 164751/1984)].

DISCLOSURE OF THE INVENTION

The present inventors, with a specific view to further improving the process, carried out repeated research, and found that diaryl or triaryl based polycyclic aromatic hydrocarbons remaining liquid at ambient temperature and showing a boiling point of not less than 250° C. can produce excellent effects under conditions of an added aromatic hydroxy compound. The finding has led to the completion of this invention.

This invention is directed to a process for selectively producing aromatic hydroxycarboxylic acids, characterized in that the said process comprises allowing a liquid mixture consisting of a polycyclic aromatic hydrocarbon, alkali metal salt of an aromatic hydroxy compound and free aromatic hydroxy compound to undergo reaction with carbon dioxide.

The present invention can achieve the following effects:

(1) The media of this invention can suspend thoroughly alkali metal salts of aromatic hydroxy compounds, which permits the complete dehydration of such alkali metal salts of aromatic hydroxy compounds to be performed promptly and at relatively low temperatures. Consequently, therecan be easily obtained anhydrous alkali metal salts of aromatic hydroxy compounds as a raw material, which, when admixed with aromatic hydroxy compounds and the reaction medium and subjected to a reaction with carbon dioxide, contribute to outstandingly improved yields of the objective compound to be obtained in such a reaction.

(2) A mixture consisting of an anhydrous alkali metal salt of aromatic hydroxy compound, aromatic hydroxy compound and a reaction medium has their components all kept in the liquid form and suspended thoroughly and uniformly under reaction conditions, and can be transported in a quantitative manner, which secures the constant reaction yield in the continuous production process.

(3) The improvement of both yield and selectivity is of utmost importance in the Kolbe-Schmitt reaction, where the production of isomers is always involved and basically inevitable owing to the principle of orientation in the aromatic substitution reaction. In the conventional Kolbe-Schmitt reaction processes, the production of isomers takes place, in spite of the reaction conditions, inclusive of temperature and pressure, being optiomally set to minimize the isomer production. However, this invention constitutes a process which keeps the starting material system in the liquid form under reaction conditions and consequently suppresses markedly the production of isomers, permitting the objective compound to be formed in the outstandingly improved selectivity, as compared with the solid-liquid suspension system in the conventional processes.

Thus, in the said reaction where aromatic hydroxycarboxylic acids are formed, the supplementary addition of an aromatic hydroxy compound allows the mutual affinity among three compounds of the aromatic hydroxy compound, the alkali metal salt of an aromatic hydroxy compound and the reaction medium to be optimally regulated, which can control the orientation direction in the said reaction and can also enhance outstandingly the selectivity.

(4) The reaction media exhibit a high degree of affinity not only for aromatic hydroxy compounds but also for alkali metal salts of aromatic hydroxy compounds, and when mixed with them to form a liquid-liquid mixture of the three components, provide a highly good suspension state, resulting in improvement in the rate of reaction step and the yield of the objective compound.

(5) The process of this invention, which suppresses the conversion into tar of the reaction product in the reaction step and allows the tarry by-products to dissolve in the reaction medium layer, minimizes the contamination of tarry substances into a layer of the alkali metal salt of aromatic hydroxy compound, thus preventing reductions in reaction rate and in yield and proportion of the desired compound owing to contamination of tarry substances.

(6) The above-described reaction media, because of their increased distribution ratio for aromatic hydroxy compounds, allow aromatic hydroxy compounds to migrate into the water layer to a minimal extent, and consequently facilitate the recovery of aromatic hydroxy compounds. This, coupled with a reduced degree of contamination of tarry substances into the water layer, eliminates the extraction step with organic solvents, etc. for the water layer in the finishing treatment step, while securing the direct production of the objective compound from the water layer.

(7) The above-mentioned reaction media demonstrate excellent thermal stability at increased temperatures even in the presence of alkali metal salts of aromatic hydroxy compounds. Since the loss as a result of thermal degradation is small, it is economically advantageous.

(8) The aforesaid reaction media not only enhances the yield and percentage obtained of the intended product, but also since the media themselves possess superior thermal stability, the production of impurities is reduced, and this facilitates the treatment procedure in the finishing treatment step.

(9) The above-described reaction media, with their higher boiling points, usually bring about no pressure increase owing to vapour pressure of solvent in the reaction step, and offer consequently additional advantage that the reaction vessel can be designed to withstand merely the pressure of carbon dioxide.

The polycyclic aromatic hydrocarbons which are used in this invention include, for example, diaryls, diarylalkanes, triaryls, triarylalkanes or their hydrogenated compounds or mixtures thereof; as preferred examples, among others, there may be mentioned 1-phenyl-1-(2,3-dialkylphenyl)-alkanes, triphenyl, dibenzyltoluene, hydrogenated triphenyls or mixtures thereof, and those having a boiling point of not less than 250° C. are desirable.

The alkali metal salts of aromatic hydroxy compounds include, for example, potassium phenolate, sodium phenolate or sodium 2-naphtholate.

In the Kolbe-Schmitt reaction process, the complete dehydration of a raw material, an alkali metal salt of aromatic hydroxy compound, constitutes one of the most important problems, and inadequate dehydration of the above-described raw material results in a marked decrease in reaction yield. The above raw material can be produced in accordance with the conventional method by the reaction of phenol or 2-naphthol with an alkaline potassium or sodium compound, such as hydroxides, carbonates and hydrogencarbonates of potassium or sodium, and it is particularly advantageous to dehydrate the resulting alkali metal salt of aromatic hydroxy compound in the presence of the above-mentioned reaction medium.

According to this invention, the reaction of an alkali metal salt of aromatic hydroxy compound with carbon dioxide is carried out at a temperature of not lower than 100° C., preferably 120° to 300° C., particularly 150° to 300° C., and at a carbon dioxide pressure of not higher than 30 kg/cm$^2$ (G), preferably 1 to 15 kg/cm$^2$ (G), particularly 2 to 10 kg/cm$^2$ (G). The addition amount of the aromatic hydroxy compound is normally not less than 0.05 mole per mole of alkali metal salt of aromatic hydroxy compound, preferably 0.1 to 2 mole. The usage amount of the reaction medium is normally not less than 0.5 part by weight against each part by weight of alkali metal salt of aromatic hydroxy compound, preferably 0.5 to 10 parts by weight, particularly 1 to 5 parts by weight. The reaction can be conducted either by the batch or continuous process, but it is desirable to carry out the reaction by the continuous process. As the reaction time or the residence time, there can be suitably selected any length of time ranging from several minutes to 15 hours, preferably 10 minutes to 10 hours, particularly 20 minutes to 10 hours.

The finishing treatment can be conducted, for example, by the following procedure. After addition of water to the reaction mixture, the reaction medium layer is separated out, and the dissolved aromatic hydroxy compound can be recovered with a solution of an alkaline potassium or sodium compound as an alkali metal salt of the aromatic hydroxy compound, which is then subjected to reuse. The separated water layer is adjusted in liquid nature with dilute or concentrated sulfuric acid, and the dissolved aromatic hydroxy compound is then extracted with use of toluene or xylene as a reaction medium or organic solvent, as the case may be. The organic solvent layer is washed with a solution of an alkaline potassium or sodium compound to recover it as an alkali metal salt of the aromatic hydroxy compound for reuse as a starting compound. Alternatively, the whole amount of the organic solvent layer can be distilled off to separate into the organic solvent and the aromatic hydroxy compound, with the latter being reused as a starting compound. These finishing treatment procedures can be suitably selected.

INDUSTRIAL UTILIZABILITY

The present invention can offer various advantages as described above under the items (1) through (9), and is of outstandingly great, industrial value.

PREFERRED MODE OF CARRYING OUT THE PRESENT INVENTION

EXAMPLE 1

Figure 1:
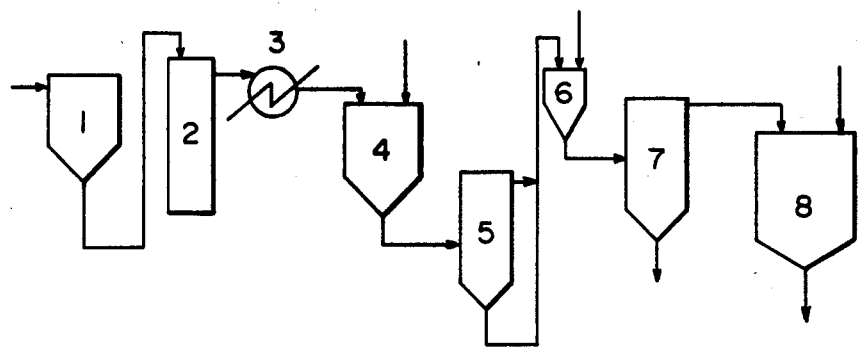
FIG. 1 is a schematic flow diagram illustrating the mode of carrying out this invention, wherein the reference numerals 1 and 4 each designate a stirring tank; the numeral 2 a reaction vessel; the numeral 3 a heat exchanger; the numeral 5 a separating tank; the numeral 6 a pH adjustment tank; the numeral 7 an extractor; and the numeral 8 an acid precipitation tank, respectively.

In a pressure reaction vessel were charged 100 g of sodium phenolate, 35 g of phenol and 400 g of a mixture of hydrogenated triphenyls, and a reaction was allowed to proceed at 250° C. and at a carbon dioxide pressure of 7 kg/cm$^2$ (G) for 20 minutes, with stirring The reaction mixture was cooled and charged into 200 ml of water, followed by separation into the reaction medium layer and the water layer at 60° C. The water layer was extracted with 50 g of xylene, and the phenol was recovered with an aqueous potassium hydroxide solution from the reaction medium and extraction medium layers. After recovery of phenol, the water layer was made acid with dilute sulfuric acid to give 80.8 g of p-hydroxybenzoic acid (having a purity of 100%), with neither salicylic acid nor isophthalic acid being detected as an isomer. The yield based on potassium phenolate was 77.3%, and the recovered phenol was 21.8 g, with the selectivity being 99.7%.

EXAMPLE 2

In a pressure reaction vessel were charged 100 g of sodium phenolate, 40 g of phenol and 400 g of 1-phenyl-1-(2,3-dimethylphenyl)-ethane, and a reaction was allowed to proceed at 170° C. and at a carbon dioxide pressure of 10 kg/cm$^2$(G) for 2 hours, with stirring. The reaction mixture was cooled and charged into 500 ml of water, followed by separation into the reaction medium layer and the water layer at 90° C. The water layer was extracted with 50 g of xylene, and the phenol was recovered with an aqueous sodium hydroxide solution from the reaction medium and extraction medium layers. After recovery of phenol, the water layer was made acid with dilute sulfuric acid to give 94.3 g of salicylic acid, with neither p-hydroxybenzoic acid nor isophthalic acid being detected as an isomer. The yield based on sodium phenolate was 90.2%, and the recovered phenol was 57 g, with the selectivity being 98.5%.

EXAMPLE 3

In a pressure reaction vessel were charged 166 g of sodium 2-naphtholate, 72 g of 2-naphthol and 498 g of hydrogenated triphenyl, and a reaction was allowed to proceed at 260° C. and at a carbon dioxide pressure of 5 kg/cm$^2$(G) for 3 hours, with stirring. The reaction mixture was charged into 800 ml of water, and the resulting mixture was adjusted to a pH 5.5 with sulfuric acid, followed by separation into the reaction medium layer and the water layer at 85° C. The 2-naphthol was recovered with an aqueous sodium hydroxide solution from the reaction medium layer. After recovery of 2-naphthol, the water layer was adjusted to a pH 2.0 with sulfuric acid at the same temperature, cooled to 40° C. and subjected to filtration to give 89.3 g of 2-hydroxynaphthalene-3-carboxylic acid. The product was found to contain only 0.1% of 2-hydroxynaphthalene-6-carboxylic acid, with no trace of 2-hydroxynaphthalene-1-carboxylic acid. The yield based on sodium 2-naphtholate was 47.5%, with the selectivity being 99.3%.

EXAMPLE 4

A finishing treatment was carried out continuously, while employing the facilities as shown in the drawing. On an hourly basis, 83 kg of sodium 2-naphtholate, 42 kg of 2-naphthol and 166 kg of a mixture of hydrogenated triphenyls were fed to a stirring tank 1, followed by stirring and suspension. The resulting suspension mixture was supplied at a rate of 291 kg/hr to a reaction vessel 2 maintained at a carbon dioxide pressure of 6 kg/cm$^2$(G), and a reaction was allowed to proceed at 260° C., with the residence time being kept at 3 hours. The reaction mixture flowing out of the reaction vessel 2 was cooled with a heat exchanger 3, and mixed with water fed at a rate of 420 l/hr in a stirring tank 4, and the resulting mixture was regulated at a temperature of 85° C. and transferred to a separating tank 5, followed by separation into the reaction medium layer and the water layer at 85° C. From the upper reaction medium layer, the 2-naphthol was recovered as sodium naphtholate with use of a recovery apparatus (not shown in the drawing). The lower water layer was adjusted in a pH adjusting tank 6 to a pH 5.5 with dilute sulfuric acid and transferred to an extractor 7, where the 2-naphthol and tar were extracted with 2000 liters of xylene. From the xylene layer, there were recovered the xylene and 2-naphthol by use of a vacuum distillation apparatus (not shown in the drawing). The water layer flowing out of the extactor 7 was transferred to an acid precipitation tank 8, and adjusted to a pH 2.0 with dilute sulfuric acid at 85° C. to perform acid precipitation, whereby there was produced 2-hydroxynaphthalene-3-carboxylic acid at a rate of 44.8 kg/hr. The yield based on sodium 2-naphtholate was 47.7%, and 2-naphthol was recovered at a rate of 37.3 kg/hr, with the selectivity being 99.4%.

EXAMPLE 5

In a pressure reaction vessel were charged 100 g of potassium phenolate, 35 g of phenol and 500 g of a mixture of hydrogenated triphenyls, and a reaction was allowed to proceed at 250° C. and at a carbon dioxide pressure of 7 kg/cm$^2$(G) for 20 minutes, with stirring. The reaction mixture was cooled and charged into 200 ml of water, followed by separation into the reaction medium layer and the water layer at 60° C. The water layer was made acid with dilute sulfuric acid to give 81.6 g of p-hydroxybenzoic acid (having a purity of 99%). The yield based on potassium phenolate was 77.3%, and the recovered potassium phenolate was 21.0 g, with the selectivity being 99.7%.

What is claimed is:

1. A process for producnig p-hydroxybenzoic acid or 2-hydroxynaphthalene-3-carboxylic acid which comprises reacting a liquid mixture consisting of (A) potassium phenolate or sodium β-naphtholate, (B) free phenol or free β-naphthol and (C) a triphenyl or a hydrogenated triphenyl wherein the molar ratio of (B) to (A) is 0.1 to 2.0 and the weight ratio of (C) to (A) is 1 to 5 with carbon dioxide, said liquid mixture being maintained in the liquid state throughout the reaction with carbon dioxide.

2. The process of claim 1 for producing p-hydroxybenzoic acid wherein the liquid mixture consists of (A) potassium phenolate, (B) phenol and (C) triphenyl or hydrogenated triphenyl.

3. The process of claim 1 for producing 2-hydroxynaphthalene-3-carboxylic acid wherein said liquid mixture consists of (A) sodium β-naphtholate, (B) free β-naphthol and (C) triphenyl or hydrogenated triphenyl.

4. The process of claim 1 which further comprises after conclusion of said reaction, separating the triphenyl or hydrogenated triphenyl reaction medium containing unreacted potassium phenolate or sodium β-naphtholate dissolved therein and recovering the dissolved potassium phenolate or sodium β-naphtholate.

5. The process of claim 1 which further comprises, after conclusion of said reaction, adding water to the reaction mixture, adjusting the pH of the resulting mixture to separate a water layer having the free phenol or free β-naphthol dissolved therein, and extracting the phenol or β-naphthol with an organic solvent.

* * * * *